United States Patent [19]

Berthelsen et al.

[11] Patent Number: 5,002,067

[45] Date of Patent: Mar. 26, 1991

[54] MEDICAL ELECTRICAL LEAD EMPLOYING IMPROVED PENETRATING ELECTRODE

[75] Inventors: Wendy A. Berthelsen, South Range, Mich.; Kenneth B. Stokes, Minneapolis, Minn.

[73] Assignee: Medtronic, Inc., Minneapolis, Minn.

[21] Appl. No.: 398,349

[22] Filed: Aug. 23, 1989

[51] Int. Cl.$^5$ ............................................. A61N 1/05
[52] U.S. Cl. .................................. 128/786; 128/642; 128/419 P
[58] Field of Search ............... 128/642, 783, 784, 785, 128/786, 802, 419 P

[56] References Cited

U.S. PATENT DOCUMENTS

| | | | |
|---|---|---|---|
| H356 | 11/1987 | Stokes et al. | 128/785 |
| 3,750,650 | 8/1973 | Ruttgers | 128/642 |
| 3,804,080 | 4/1974 | Ruttgers et al. | 128/642 |
| 4,180,080 | 12/1979 | Murphy | 128/642 |
| 4,577,642 | 3/1986 | Stokes | 128/784 |
| 4,606,118 | 8/1986 | Cannon et al. | 29/825 |
| 4,644,957 | 2/1987 | Ricciardelli et al. | 128/784 |
| 4,711,251 | 12/1987 | Stokes | 128/784 |

*Primary Examiner*—Lee S. Cohen
*Assistant Examiner*—Scott M. Getzow
*Attorney, Agent, or Firm*—Reed A. Duthler

[57] ABSTRACT

A cardiac pacing lead or other stimulation lead carrying a drug compounded into a matrix, located within the distal portion of the lead. The drug is delivered to the tissue adjacent the distal end of the lead. In connection with the polymer matrix, the lead is provided with a penetrating electrode, which takes the form of a sharpened helix. The electrode is provided with a groove, running the length of the electrode and exposed to the matrix. In use, the drug elutes out of the matrix, through the groove in the electrode, and into the tissue to be stimulated. The drug may be an antiinflammatory agent, such as a glucocorticosteroid, to minimize the effects of implantation of the electrode into the tissue to be stimulated.

7 Claims, 1 Drawing Sheet

MEDICAL ELECTRICAL LEAD EMPLOYING IMPROVED PENETRATING ELECTRODE

BACKGROUND OF THE INVENTION

The present invention relates generally to electrical medical leads, and more particularly to stimulation leads of the type which dispense a steroid or other drug adjacent the stimulation site. The invention is particularly useful in the context of a cardiac pacing lead.

Delivery of a drug at the stimulation site of an implantable pacing lead is disclosed in U.S. Pat. No. 4,711,251, issued to Stokes. A particularly desirable configuration for such a lead is disclosed in U.S. Pat. No. 4,506,680, also issued to Stokes. In this configuration, the drug to be dispensed, a glucocorticosteroid, is compounded with silicone rubber based medical adhesive, and located within a chamber within the distal end of the stimulation electrode. The steroid acts as an anti-inflammatory agent, reducing the effects of inflammation due to the reaction of the tissue to the stimulation electrode.

Alternative embodiments of stimulation electrodes which elute a steroid or other drugs are disclosed in U.S. Pat. No. 4,606,118 issued to Cannon et al and in U.S. Pat. No. 4,577,642 issued to Stokes. A myocardial pacing lead adapted to deliver steroid at the stimulation site is disclosed in Statutory Invention Registration No. H0356, by Stokes et al in which a steroid is delivered through a barbed electrode to a delivery point within the myocardium.

SUMMARY OF THE INVENTION

The lead disclosed in Statutory Invention Registration No. H0356 by Stokes et al proposes the use of a hollow electrode through which a steroid or other drug may be dispensed. The steroid is either compounded in the electrode itself, or located within the body of the lead adjacent the electrode. However, the need for an adequate passageway for drug elution through such an electrode must be balanced against the necessity for structural strength. The larger the bore, the thinner the outer walls, and the less structural strength the fixation helix will have.

In the present invention, the fixation helix, or other fixation device, such as a barb or a hook, is provided with a longitudinal groove, not unlike the groove found in the teeth of certain venomous snakes. Because the groove may be machined from the outside of the wire used to fabricate the fixation helix, its cross sectional area can be accurately controlled. The groove is typically applied to the wire first, and the wire subsequently coiled to form the fixation helix. In embodiments in which the wire is grooved first and then coiled, it may be desirable to coil the wire such that the groove is located on the medial or lateral edge of the wire, as coiled, rather than being located on the inner or outer surface of the coil. This orientation is believed to assist in avoiding collapse of the groove during winding.

In use, the fixation helix is implanted within muscle tissue. Muscle tissue adjacent the groove effectively forms part of the outer wall of the passage along which drug is eluted. As a result, for a given desired elution passage size and wire diameter, a helix according to the present invention will have a relatively greater portion of its cross section formed of the metallic material than a correspondingly sized coiled tube. In addition, because the groove runs the length of the fixation helix, elution of the drug all along the length of the helix is facilitated, rather than limiting elution of the drug to the tip of the helix or to individual pores or apertures along the length of the helix. This is believed to provide a faster drug elution rate for a given bore size than a corresponding tubular structure.

In the embodiment illustrated, the drug to be eluted is a glucocorticosteroid compounded in a polymer matrix such as a hydrogel, silicone rubber, or other polymer. In the configuration illustrated, the groove on the fixation helix extends into the polymeric matrix holding the drug, allowing the drug to be eluted into the groove of the fixation helix, and thence into the tissue in which the fixation helix is embedded.

BRIEF DESCRIPTION OF THE DRAWING

The FIGURE is a side, cutaway view through the distal end of a lead according to the present invention.

DETAILED DESCRIPTION OF THE INVENTION

Figure 1:
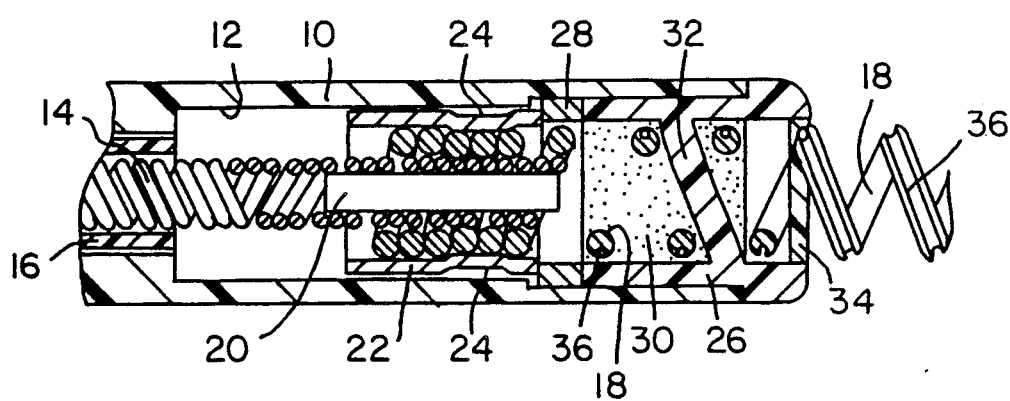

FIG. 1 is a side, cutaway view of the distal end of a cardiac pacing lead employing a monolithic controlled release device according to the present invention. The structure of the proximal portion of the lead may correspond to that illustrated in the article "The Impact of Pending Technologies on a Universal Connector Standard", by Doring and Flink, published in *PACE*, Nov.--Dec. 1986, part 2, pp. 1186-1190, incorporated herein by reference in its entirety. Additional appropriate configurations for the proximal end of the pacing lead are disclosed in U.S. Pat. application Ser. No. 304,756, for a "MEDICAL ELECTRICAL LEAD CONNECTOR", by Ufford et al, filed Jan. 31, 1989, also incorporated herein by reference in its entirety. Alternatively, any other conventional pacing lead construction may be used, so long as it provides for a free member extending through the lead body, engageable with the helix 18.

The distal end of the pacing lead illustrated in FIG. 1 comprises an electrode assembly. This assembly includes a molded plastic electrode head 10, which has an internal cylindrical lumen 12. Entering the lumen 12 from the proximal end is an elongated coiled conductor 14. As illustrated, conductor 14 takes the form of a multifilar coil having three individual filars. However, other coil configurations might also be used. Surrounding coil 14 is a tubular insulative sheath 16, which extends to the proximal end of the lead. Coil 14 is mounted so that it rotates freely within sheath 16. Exiting the distal end of the lead is a helix 18, which is screwed into the tissue to be stimulated and functions as an electrode. Helix 18 and coil 14 are mechanically and electrically maintained in contact with one another by means of crimps 24, which mechanically compress the proximal end of helix 18 and the distal end of coil 14 between crimping core 20 and crimping sleeve 22.

As coiled conductor 14 is rotated in a counterclockwise direction, as viewed from the distal end of the lead, helix 18 is screwed out of the distal end of electrode head 10, rotating around electrode guide 26. A radiopaque indicator ring 28 is located within lumen 12 of electrode head 10, and serves to indicate the position of helix 18. By using a fluoroscope, the physician can determine the distance between crimping sleeve 20 and indicator ring 28, and thereby determine the distance helix 18 has been screwed out of the electrode head 10.

A monolithic controlled release device 30 (MCRD) is located within electrode guide 26. MCRD 30 takes the form of a cylindrical plug having a spiral lumen through which electrode 18 may rotate. MCRD 30 is retained within the interior of electrode guide 26 by means of cross bar 32, which extends through MCRD 30. Cross bar 32 also serves as a guide for the rotation of electrode 18.

In the disclosed embodiment, the distal end of the lead is insulative, and electrode 18 serves as the stimulating electrode. However, alternative embodiments of the invention are believed possible in which helix 18 is insulated from conductor 14 and used only to affix the distal end of the lead to heart tissue. In such embodiments, an electrode would be mounted to the distal end of the lead and coupled to conductor 14. Leads employing such configurations are disclosed in U.S. Pat. No. 4,217,913 issued to Dutcher and in U.S. Pat. No. 4,209,019 issued to Dutcher et al, both of which are incorporated herein by reference in their entirety. Located at the distal end of electrode guide 26 is a retainer disk 34 which includes an eccentrically located hole through which helix 18 passes. Retainer disk 34 is an optional component which is desirable when the polymer matrix chosen for MCRD 30 exhibits substantial swelling, and functions to retain the MCRD within the distal end of electrode guide 26.

In operation, it is anticipated that the lead will be passed through the venous system into the right ventricle of the heart. When properly located, helix 18 will be screwed out of the distal end of the lead and into the tissue of the heart. This will retain the distal end of electrode guide 26 against the heart tissue.

MCRD 30 may be fabricated of a silicone based polymer, as disclosed in the above-cited Stokes et al application, or may be fabricated of other polymers. MCRD 30 preferably incorporates an antiinflammatory drug which may be, for example, the sodium salt of dexamethasone phosphate. Because MCRD 30 is retained within electrode guide 26 and because helix 18 holds the end of electrode guide 26 adjacent heart tissue, migration of the drug contained in MCRD 30 is limited to the tissue in contact with the distal end of electrode guide 26. In embodiments which dispense with retainer disk 34, direct elution out of MCRD 30 into contact with the heart tissue will be limited generally to the tissue within the circular area defined by the lumen through electrode guide 26. In embodiments employing a retainer disk 34, the elution area will be limited primarily to the helix 18.

In either embodiment, it is believed valuable to employ a helix 18 which is provided with a longitudinal groove 36. Steroid eluted from MCRD 30 passes down elongated groove 36, and is dispensed along the groove to the tissue surrounding helix 18. This provides delivery of the drug directly to the site of stimulation. Groove 36 may be machined into a metal wire, and the wire subsequently wound to form a helix 18 or a groove may be machined into helix 18 after winding. Groove 36, in conjunction with the tissue surrounding helix 18, will provide a lumen through which drug may pass.

Although the embodiment illustrated takes the form of a unipolar lead, a bipolar lead of similar configuration is believed to be within the scope of the claims of the invention. For example, a ring electrode as illustrated in the above cited article by Doring et al may be employed, or any other conventional ring electrode structure known to the art. Although the preferred embodiment of the invention employs an advanceable, rotatable helix, the invention is also believed valuable in the context of a screw-in lead having a fixed helix. In general, the above disclosure should be considered exemplary, rather than limiting with regard to the scope of the following claims.

We claim:

1. A medical electrical lead comprising:
   an elongated insulative lead body having a proximal end and a distal end;
   an elongated conductor having a proximal end and a distal end and mounted within said insulative lead body; and
   an electrode assembly having a proximal end and a distal end and having a drug release means located within said electrode assembly for release of a therapeutic drug, said electrode assembly further comprising fixation means extending from said electrode assembly for holding said electrode assembly adjacent body tissue, an outer surface of said fixation means provided with an elongated groove, a proximal end of said groove exposed to said drug release means a distal end of said groove extending from the distal end of said electrode assembly whereby when said fixation means is inserted into said body tissue, said elongated groove in conjunction with said body tissue define a passage along which said drug released by said drug release means may pass, and thereby pass into said body tissue, said electrode assembly further comprising a conductive electrode surface electrically coupled to the distal end of said elongated conductor.

2. A lead according to claim 1 wherein said electrode surface is located on said fixation means.

3. A lead according to claim 1 or claim 2 wherein said fixation means extends proximally into said drug release means and wherein said groove on said fixation means also extends into said drug release means, and wherein said drug release means comprises a solid matrix in which said drug is compounded, and from which said drug elutes into said groove of said fixation means.

4. A medical electrical lead comprising:
   an elongated insulative lead body having a proximal end and a distal end;
   an elongated conductor having a proximal end and a distal end and mounted within said insulative lead body; and
   an electrode assembly having proximal end and a distal end and having a drug release means located within said electrode assembly for release of a therapeutic drug, said electrode assembly further comprising fixation means extending from said electrode assembly for holding said electrode assembly adjacent body tissue, said fixation means provided with an elongated groove, a proximal end of said groove exposed to said drug release means, a distal end of said groove extending from the distal end of said electrode assembly whereby when said fixation means is inserted into said body tissue, said elongated groove in conjunction with said body tissue defines a passage along which said drug released by said drug release means may pass, and thereby pass into body tissue, said electrode assembly further comprising a conductive electrode surface electrically coupled to the distal end of said elongated conductor and wherein said fixation means comprises a fixation helix which may be advanced out of the distal end of said electrode assembly or retracted into the distal end of said electrode assembly, said lead further comprising means for advancing and retracting said fixation helix.

5. A lead according to claim 4 wherein said fixation helix is advanced out of and retracted into the distal end of said electrode assembly by rotating said fixation helix and wherein said means for advancing and retracting said fixation helix comprises means for rotating said fixation helix.

6. A lead according to claim 5 wherein said means for advancing and retracting said fixation helix comprises said elongated conductor, said elongated conductor rotatably mounted within said insulative lead body.

7. A lead according to claim 5 wherein said fixation helix extends through and rotates through said drug release means and wherein said elongated groove on said fixation helix extends into said drug release means when said helix is advanced from the distal end of said electrode assembly.

* * * * *